United States Patent
Gao et al.

(10) Patent No.: US 12,070,417 B2
(45) Date of Patent: Aug. 27, 2024

(54) OPHTHALMIC FLUIDICS SYSTEM WITH EDDY CURRENT PRESSURE SENSOR

(71) Applicant: Alcon Inc., Fribourg (CH)

(72) Inventors: Shawn X. Gao, Irvine, CA (US); Ivan Milutinovic, San Marcos, CA (US); Roderick S. Van, Long Beach, CA (US); Vincent A Baxter, Temecula, CA (US); Raphael Gordon, Ladera Ranch, CA (US)

(73) Assignee: Alcon Inc., Fribourg (CH)

( * ) Notice: Subject to any disclaimer, the term of this patent is extended or adjusted under 35 U.S.C. 154(b) by 389 days.

(21) Appl. No.: 16/858,925

(22) Filed: Apr. 27, 2020

(65) Prior Publication Data

US 2020/0353133 A1    Nov. 12, 2020

Related U.S. Application Data

(60) Provisional application No. 62/843,841, filed on May 6, 2019.

(51) Int. Cl.
*A61F 9/007*    (2006.01)
*A61M 1/00*     (2006.01)

(52) U.S. Cl.
CPC .......... *A61F 9/00745* (2013.01); *A61F 9/007* (2013.01); *A61M 1/73* (2021.05);
(Continued)

(58) Field of Classification Search
CPC .. A61F 9/00745; A61F 9/00736; A61F 9/007; A61M 1/0058; A61M 2210/0612;
(Continued)

(56) References Cited

U.S. PATENT DOCUMENTS

| | | | |
|---|---|---|---|
| 4,369,780 A | * | 1/1983 | Sakai ................... A61M 39/281 200/81.9 R |
| 4,671,116 A | | 6/1987 | Glennon et al. |

(Continued)

FOREIGN PATENT DOCUMENTS

| | | |
|---|---|---|
| CN | 108463259 A | 8/2018 |
| RU | 54772 U1 | 7/2006 |

(Continued)

OTHER PUBLICATIONS

"Glossary: Eddy current." Micro-Epsilon-America. Accessed 2022. <https://www.micro-epsilon.com/service/glossar/Wirbelstrom.html> (Year: 2022).*

*Primary Examiner* — Scott J Medway
(74) *Attorney, Agent, or Firm* — Patterson + Sheridan, LLP

(57) ABSTRACT

Systems and methods are disclosed for measuring fluid pressure in an ophthalmic surgical system. An example system comprises a fluid flow path and a pressure sensor system for measuring pressure in the fluid flow path. The pressure sensor system comprises a conductive, movable diaphragm having a first side and a second side, the first side of the diaphragm facing the fluid flow path, and an eddy current position sensor positioned on the second side of the diaphragm without contacting the diaphragm. The eddy current position sensor comprises a position sensor coil activatable by high frequency alternating current and signal conditioning electronics capable of sensing inductance or impedance or resonant frequency variation in the position sensor coil as a gap between the diaphragm and the position sensor coil changes and of translating that variation into a displacement signal correlated to fluid pressure. A method of measuring fluid pressure may be performed using one or more of the systems described herein.

20 Claims, 5 Drawing Sheets

(52) U.S. Cl.
CPC ....... *A61M 1/77* (2021.05); *A61M 2205/3317* (2013.01); *A61M 2205/3337* (2013.01); *A61M 2205/702* (2013.01)

(58) Field of Classification Search
CPC .... A61M 1/74; A61M 2205/12; A61M 1/774; A61M 2205/3317; A61M 2205/3337; A61M 2205/702; A61M 1/77; A61P 27/02; A61P 27/12; A61B 2217/005; A61B 2217/007; G01L 9/007; G01L 9/0072; G01L 1/14; G01L 1/127
See application file for complete search history.

(56) References Cited

U.S. PATENT DOCUMENTS

| | | | |
|---|---|---|---|
| 5,261,883 A * | 11/1993 | Hood | A61M 3/0212 606/107 |
| 5,279,163 A * | 1/1994 | D'Antonio | G01L 19/0007 73/728 |
| 5,470,312 A | 11/1995 | Zanger et al. | |
| 5,910,110 A | 6/1999 | Bastable | |
| 6,261,283 B1 | 7/2001 | Morgan et al. | |
| 6,293,926 B1 | 9/2001 | Sorensen et al. | |
| 6,572,349 B2 | 6/2003 | Sorensen et al. | |
| 6,632,214 B2 | 10/2003 | Morgan | |
| 6,740,074 B2 | 5/2004 | Morgan | |
| 6,902,542 B2 | 6/2005 | Gordon | |
| 6,962,488 B2 | 11/2005 | Davis et al. | |
| 7,393,189 B2 | 7/2008 | Davis et al. | |
| 8,011,905 B2 | 9/2011 | Artsyukhovich | |
| 8,545,198 B2 | 10/2013 | Artsyukhovich | |
| 8,721,594 B2 * | 5/2014 | Zacharias | A61M 1/743 604/35 |
| 8,790,096 B2 | 7/2014 | Sorensen | |
| 9,482,216 B2 | 11/2016 | Sorensen | |
| 9,782,159 B2 * | 10/2017 | Tesar | A61B 17/0293 |
| 9,844,613 B2 | 12/2017 | Baker et al. | |
| 9,931,447 B2 | 4/2018 | Layser | |
| 2004/0074281 A1 * | 4/2004 | Lobdell | A61M 1/73 73/1.57 |
| 2004/0104725 A1 * | 6/2004 | Sergoyan | G01B 7/105 324/225 |
| 2004/0253129 A1 * | 12/2004 | Sorensen | F04B 43/1269 417/572 |
| 2006/0144155 A1 * | 7/2006 | Liu | G01L 9/007 73/753 |
| 2009/0182266 A1 * | 7/2009 | Gordon | A61M 1/74 604/30 |
| 2010/0012395 A1 | 1/2010 | Mannhart et al. | |
| 2016/0166742 A1 * | 6/2016 | Layser | A61F 9/00745 604/32 |
| 2017/0189231 A1 * | 7/2017 | Baxter | A61M 1/77 |
| 2017/0216093 A1 | 8/2017 | Kuebler | |
| 2017/0328793 A1 * | 11/2017 | Hee | G01L 9/0072 |
| 2017/0358205 A1 * | 12/2017 | Ippolito | G08G 1/02 |
| 2018/0318503 A1 | 11/2018 | Burke | |
| 2019/0060533 A1 * | 2/2019 | Kuebler | A61M 1/77 |
| 2020/0164486 A1 * | 5/2020 | Che | H01L 21/67253 |

FOREIGN PATENT DOCUMENTS

| | | | |
|---|---|---|---|
| WO | 2011045037 A3 | 4/2011 | |
| WO | WO2011045037 A2 | 4/2011 | |
| WO | WO2014134106 A1 | 9/2014 | |
| WO | WO-2014140298 A2 * | 9/2014 | ............ G01D 5/225 |
| WO | WO2017029629 A1 | 2/2017 | |
| WO | 2017036652 A1 | 3/2017 | |

* cited by examiner

OPHTHALMIC FLUIDICS SYSTEM WITH EDDY CURRENT PRESSURE SENSOR

CROSS-REFERENCE TO RELATED APPLICATIONS

This application claims priority to and benefit of U.S. Provisional Patent Application No. 62/843,841, filed May 6, 2019, the entire contents of which are incorporated by reference herein in its entirety.

TECHNICAL FIELD

The present disclosure is directed to systems and methods relating to ophthalmic surgery and, more particularly, to monitoring fluid pressure during ophthalmic surgery.

BACKGROUND

In ophthalmic surgical procedures, fluids are often aspirated from the eye during the procedure. For example, in vitreoretinal surgery, a device may be used to aspirate vitreous material from the eye. As another example, in cataract surgery, a device may be used to fragment or emulsify a lens and to aspirate the broken or emulsified lens from the eye. In these or other procedures, a balanced salt solution (BSS) or other irrigation fluid may be introduced into the eye and removed during the procedure as part of the aspirated fluid.

In such ophthalmic surgical procedures, it can be desirable to monitor the pressure of the fluid being aspirated as it is being aspirated. This can help the operator to regulate the procedure, to monitor the intraocular pressure, and/or to determine if any partial or total occlusions are present in the aspiration line. Additionally, it can be desirable to monitor the pressure of the fluid being introduced into the eye. This too can help the operator to regulate the procedure and/or to monitor the intraocular pressure.

Prior systems for fluid irrigation and aspiration and/or pressure measurement in ophthalmic procedures are disclosed in U.S. Pat. Nos. 6,261,283, 6,293,926, 6,572,349, 6,632,214, 6,740,074, 6,902,542, 6,962,488, 7,393,189, 8,011,905, 8,545,198, 8,790,096, 9,482,216, and 9,931,447, the disclosures of which are hereby incorporated by reference herein in their entirety. Prior pressure sensors are additionally disclosed in U.S. Pat. Nos. 5,910,110 and 5,470,312, the disclosures of which are hereby incorporated by reference herein in their entirety.

Prior systems for monitoring fluid pressure during ophthalmic procedures include using a load cell to measure deflection of a diaphragm in contact with the fluid and using optical measurement of deflection of a diaphragm in contact with the fluid. The load cell system involves contact of the load cell transducer to the diaphragm on the opposite side of the diaphragm from the fluid. This contact method can have a limited frequency response and relatively high hysteresis and may require additional protection for the sensor to satisfy safety requirements. The optical system involves reflecting light off the diaphragm to measure its displacement. While this is a non-contact method, such a system can be sensitive to the optical alignment and/or surface finish variations of the diaphragm.

Accordingly, a need exists for improved systems and methods for monitoring fluid pressure in ophthalmic procedures.

SUMMARY

The present disclosure is directed to systems and methods for measuring fluid pressure in an ophthalmic surgical system.

In some embodiments, an ophthalmic surgical system comprises a handpiece with a working tip for performing an ophthalmic surgical procedure inside an eye; an irrigation system for delivering irrigating fluid to the eye during the ophthalmic surgical procedure, the irrigation system comprising an irrigation source, an irrigation path in the handpiece, and irrigation tubing between the irrigation source and the irrigation path in the handpiece; an aspiration system for aspirating fluid from the eye during the ophthalmic surgical procedure, the aspiration system comprising an aspiration path in the handpiece, aspiration tubing extending from the aspiration path in the handpiece, and a pump for providing suction through the aspiration tubing and aspiration path in the handpiece; and an eddy current pressure sensor system. In some embodiments, an example eddy current pressure sensor system comprises a conductive, movable diaphragm having a first side and a second side, the first side of the diaphragm facing a flow path either for aspiration fluid being aspirated from the eye or irrigation fluid being delivered to the eye; and an eddy current position sensor positioned on the second side of the diaphragm without contacting the diaphragm, the eddy current position sensor comprising a position sensor coil activatable by high frequency alternating current and signal conditioning electronics capable of sensing inductance or impedance variation or a resonant frequency change in the position sensor coil as a gap between the diaphragm and the position sensor coil changes and of translating that variation into a displacement signal correlated to fluid pressure.

In some embodiments, the position sensor coil is housed in a non-conductive housing. In some embodiments, the eddy current position sensor comprises a high frequency oscillator for activating the position sensor coil at a high frequency.

In some embodiments, an ophthalmic surgical system comprising a fluidics module in combination with a fluidics cassette, the fluidics module and fluidics cassette together comprising an irrigation path through which irrigating fluid is delivered to an eye during an ophthalmic surgical procedure, an aspiration path through which aspirated fluid is removed from the eye during the ophthalmic surgical procedure, and an eddy current pressure sensor system as disclosed herein.

In some embodiments, a method of measuring fluid pressure in an ophthalmic surgical system comprises passing fluid through a fluid flow path during an ophthalmic surgical procedure, wherein a conductive, movable diaphragm is positioned with a first side of the diaphragm facing the fluid flow path; activating a position sensor coil by high frequency alternating current, wherein the position sensor coil is positioned on a second side of the diaphragm without contacting the diaphragm; and sensing inductance or impedance or resonant frequency variation in the position sensor coil as a gap between the diaphragm and the position sensor coil changes due to fluid pressure changes in the fluid flow path and translating that variation into a displacement signal correlated to fluid pressure. In some embodiments, the fluid flow path may be an aspiration path. In some embodiments, the fluid flow path may be an irrigation path.

BRIEF DESCRIPTION OF THE DRAWINGS

The accompanying drawings illustrate implementations of the systems and methods disclosed herein and, together with the description, serve to explain the principles of the present disclosure.

Figure 1:
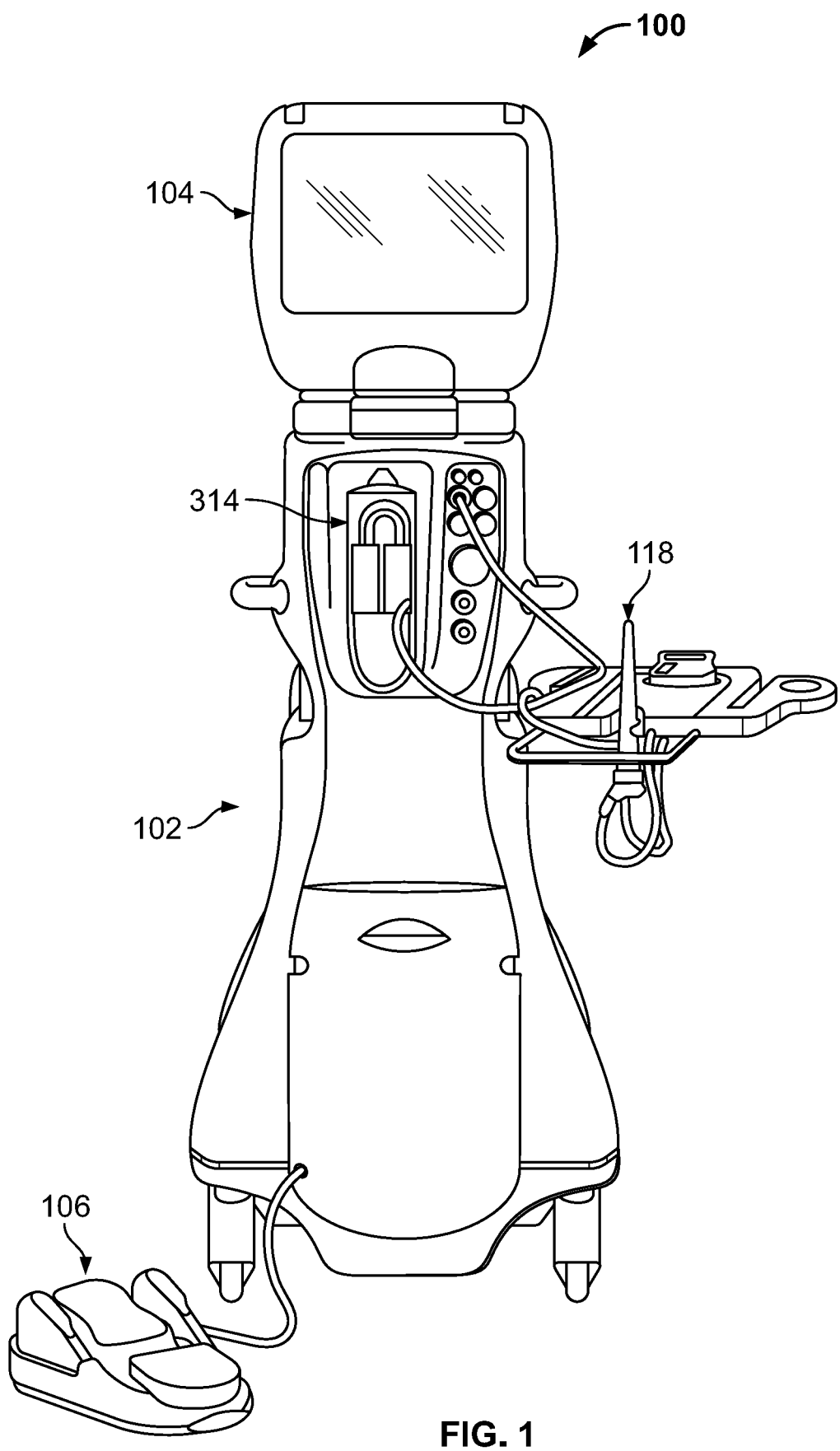
FIG. 1 illustrates an example of an ophthalmic surgical console that may be used in systems and methods in accordance with the present disclosure.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe the same. It will nevertheless be understood that no limitation of the scope of the disclosure is intended. Any alterations and further modifications to the described systems, devices, instruments, methods, and any further application of the principles of the present disclosure are fully contemplated as would normally occur to one skilled in the art to which the disclosure relates. In particular, the features, components, and/or steps described with respect to one implementation may be combined with the features, components, and/or steps described with respect to other implementations of the disclosure. For simplicity, in some instances the same reference numbers are used throughout the drawings to refer to the same or like parts.

FIG. 1 illustrates an example of an ophthalmic surgical console 100 that may be used in systems and methods in accordance with the present disclosure. The ophthalmic surgical console 100 may be similar to ophthalmic surgical consoles as shown and described in U.S. Pat. No. 9,931,447, the entire disclosure of which is hereby expressly incorporated herein by reference. The ophthalmic surgical console 100 may be similar to ophthalmic surgical consoles that have been known and used, such as the CONSTELLATION® Vision System available from Alcon Laboratories, Inc. (Fort Worth, Tex.) or the CENTURION® Vision System available from Alcon Laboratories, Inc. (Fort Worth, Tex.), or any other ophthalmic surgical console suitable for use with the principles described herein.

As shown in FIG. 1, the example ophthalmic surgical console 100 includes a housing 102 with a computer system disposed therein and an associated display screen 104 showing data relating to system operation and performance during an ophthalmic surgical procedure. The console 100 also includes a foot pedal 106 that an operator may use in controlling one or more functions.

The console 100 includes one or more systems that may be used in performing an ophthalmic surgical procedure. For example, the console 100 includes a fluidics system 200 (FIG. 2) that includes an irrigation system for delivering fluid to the eye and an aspiration system for aspirating fluid from the eye. The console 100 may also include an ultrasonic generator system for driving an ultrasonic oscillation handpiece such as for phacoemulsification during cataract surgery and/or a pneumatic vitrectomy cutter system for driving a vitrectomy handpiece. The systems may overlap and cooperate to perform various aspects of the procedures.

Figure 2:
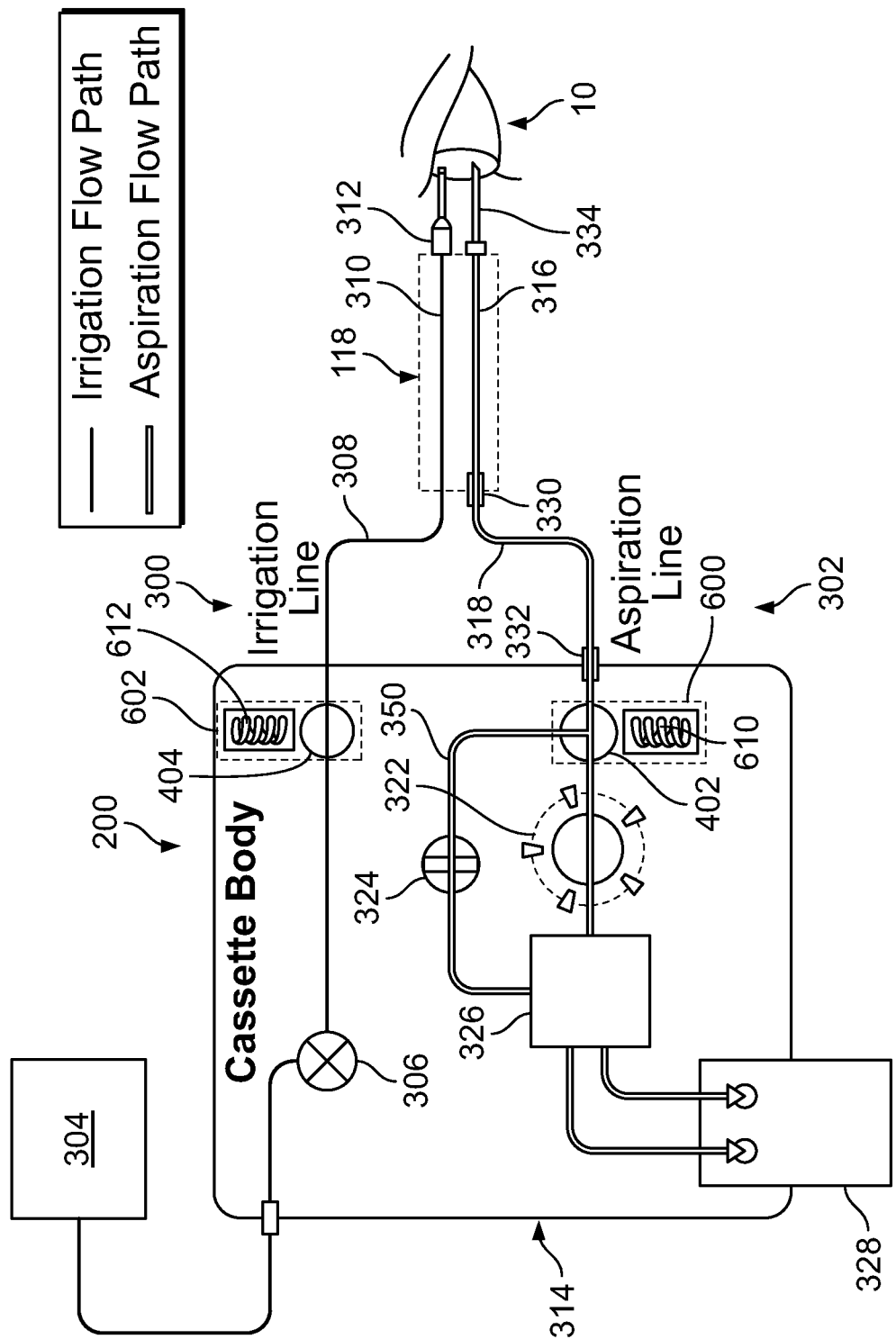
FIG. 2 is a schematic diagram of an example of a fluidics system that may be used in systems and methods in accordance with the present disclosure.

FIG. 2 is a schematic diagram of an example of a fluidics system 200 that may be used in systems and methods in accordance with the present disclosure. The fluidics system 200 may be similar to fluidics systems as shown and described in U.S. Pat. No. 9,931,447, or similar to fluidics systems that have been known and used, such as in the CONSTELLATION® Vision System or in the CENTURION® Vision System, or similar to any other fluidics system suitable for use with the principles described herein.

The fluidics system 200 includes an irrigation system 300 and an aspiration system 302, each in communication with a handpiece 118. The irrigation system 300 includes an irrigation source 304 such as a sterile solution reservoir, an irrigation valve 306 that regulates flow from the reservoir to the surgical site, flexible irrigation tubing 308, an irrigation path 310 in the handpiece 118, and a sleeve 312 that may be considered a component of the handpiece 118. The handpiece 118 includes a working tip 334 (such as a phacoemulsification tip or a vitrectomy needle), and in some embodiments the irrigation sleeve 312 may disposed about the working tip 334.

The example irrigation system 300 extends between the irrigation source 304 and the hand piece 118 and carries irrigating fluid through the irrigation flow path to the surgical site (labeled in FIG. 2 as an eye 10) during the surgical procedure. The irrigation source 304 may be a mechanically pressurized fluid source such as, for example, a clamping pressure system. In other embodiments, the irrigation source 304 may be a source suspended by a pole (e.g., an IV pole), which may or may not be adjustable. Other fluid sources may be used. In one example, the sterile fluid is a saline fluid; however, other fluids may be used.

In some embodiments, the irrigation tubing 308 is formed of multiple segments, with some segments being rigid and others being flexible. Also, in some embodiments, at least a portion of the irrigation system 300 is formed in a cassette 314 that cooperates with the console 100 in FIG. 1 to provide fluid communication between the irrigation source 304 and the patient's eye 10. The pressure of the fluid in the irrigation flow path may be monitored via a pressure sensor in the handpiece or via a pressure sensor 602 (as described below).

The example aspiration system 302 includes an aspiration path 316 in the handpiece 118, flexible aspiration tubing 318, a pump 322, a vent valve 324, a drain line reservoir 326, and a drain or drain reservoir 328. A handpiece connector 330 connects the aspiration path 316 in the handpiece 118 to the aspiration tubing 318. A cassette connector 332 connects the aspiration tubing 318 to the cassette aspiration line in the cassette 314. As can be seen, the aspiration system 302 extends from the surgical site (eye 10) to the drain reservoir 328. The aspiration system 302, including the aspiration fluid path 316, may be in fluid communication with the bore of the working tip 334 of the handpiece 118. The aspiration system 302 is used to aspirate fluid as well as any other materials to be aspirated from the eye, such as emulsified particles or vitreous fibers, through the aspiration flow path out of the eye during the surgical procedure.

In some embodiments, the aspiration tubing 318 is formed of multiple segments, with some segments being rigid and others being flexible. Also, in some embodiments, at least a portion of the aspiration system 302 is formed in the cassette 314 that cooperates with the console 100 in FIG. 1 to provide fluid communication between the handpiece 118 and the drain reservoir 328. The drain reservoir 328 may be a bag or any suitable container, and, in some embodiments, it may be a drain instead of a self-contained reservoir.

When the aspiration pathway is obstructed, such as when lens fragments enter and clog portions of the aspiration pathway during a surgery, the surgical system may detect the vacuum, or pressure difference, via a pressure sensor in the handpiece or via a pressure sensor 600 (as described below). The surgical system may control the vent valve 324 to open to relieve the vacuum or pressure difference in the aspiration pathway and to reduce the effect of the occlusion. This would reduce the magnitude of any resulting surge and maintain a predetermined level of vacuum so as not to lessen the efficiency of the procedure.

Figure 3:
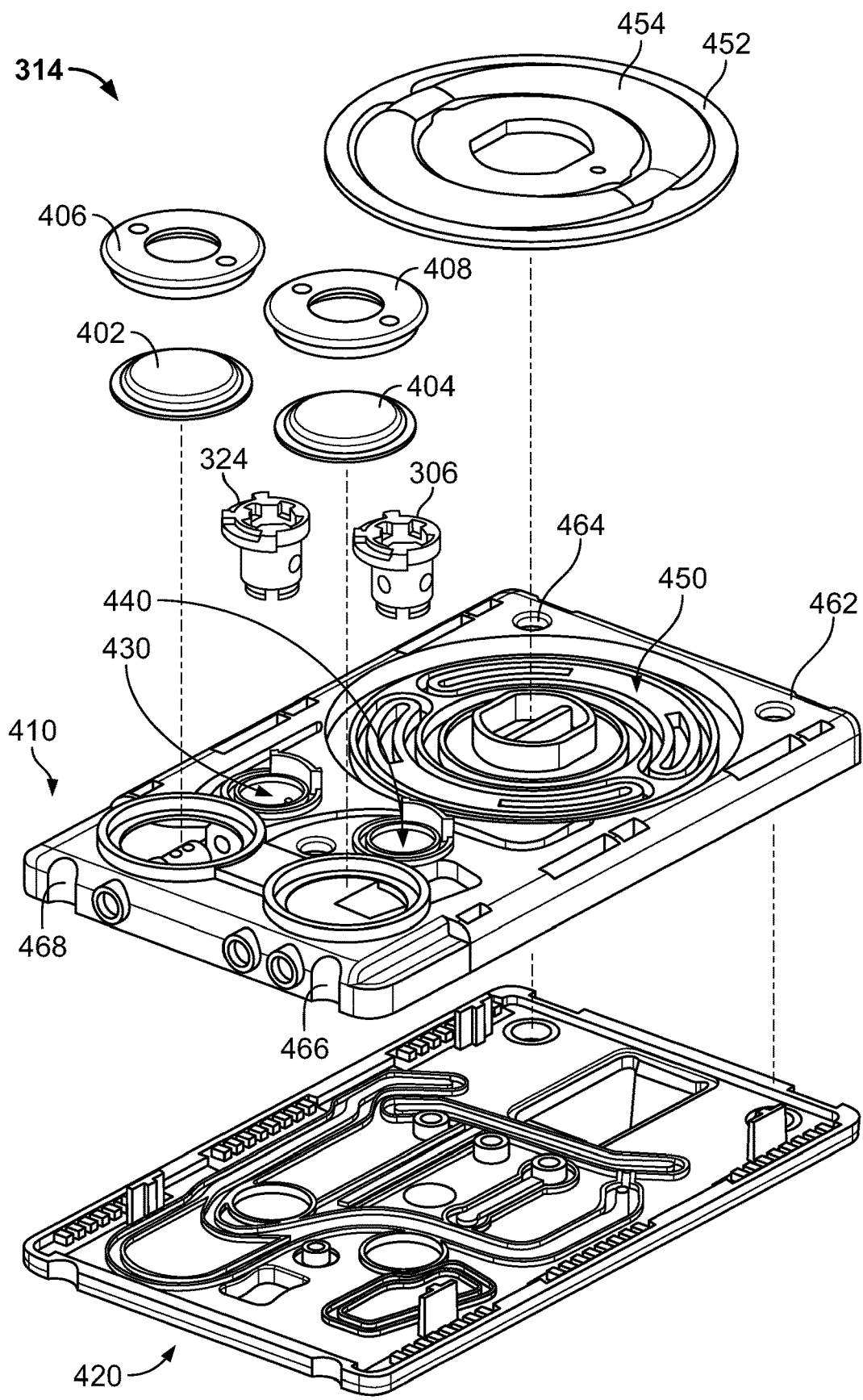
FIG. 3 illustrates an exploded view of an example of a cassette that may be used in systems and methods in accordance with the present disclosure.

FIG. 3 illustrates an exploded view of an example of a cassette 314 that may be used with the fluidics system 200 of FIG. 2 in accordance with the present disclosure. The body of cassette 314 may be formed by an upper housing 410 and a lower housing 420 coupled to each other. The housings 410 and 420 may be formed with rigid thermoplastic material, such as polycarbonate and/or polysulfone to provide rigidity and structure. A pump interface portion 450 may be disposed in cassette 314 to engage pump 322. Pump 322 may be an elastomer pump configured to drive fluid flow in the aspiration flow path. A cover 452 with an arcuate elastomeric channel cover 454 may be placed over the pump interface portion 450 as part of the pump 322. A vent valve chamber 430 and an irrigation valve chamber 440 also may be provided in the cassette 314. Vent valve chamber 430 may be configured to accommodate vent valve 324. Irrigation valve chamber 440 may be configured to accommodate irrigation valve 306.

Portions of the irrigation flow path and the aspiration flow path may extend as channels and/or tubes inside the body of the cassette 314. Vent valve chamber 430 may be positioned in a vent path 350, such that vent valve 324 may selectively close and open to allow vacuum venting via the vent path 350. In some embodiments, the vent valve 324 may be a rotary stopcock valve formed with high-density elastic polymer, such as polyethylene or acetal, such that vent valve 324 may be press-fit into vent valve chamber 430. Thus, vent valve 324 may rotate within the vent valve chamber 430 as driven by a valve motor (not shown) with an angular position encoder to selectively open and close the vent path 350.

The cassette 314 has holes 462, 464 and notches 466, 468 for aligning the cassette 314 with the console 100 when the cassette 314 is loaded into the console 100. The cassette 314 may be a removable and disposable or consumable item that can be used for a single patient procedure. A new cassette 314 may be used for a new procedure.

FIG. 3 also shows a diaphragm 402 that may be used in a pressure sensor for the aspiration system and a diaphragm 404 that may be used in a pressure sensor for the irrigation system. The diaphragm 402 is held in place in cassette 314 by a retaining ring 406. The diaphragm 404 is held in place in cassette 316 by a retaining ring 408. The retaining rings 406, 408 may be attached to the housing of the cassette 314, and the diaphragms 402, 404 may be secured between the respective retaining ring 406, 408 and the housing of the cassette 314 and/or otherwise secured to the respective retaining ring 406, 408 and/or the housing of the cassette 314, for example by adhesive or welding. The diaphragms 402, 404 and their functions in a pressure sensor are described further below.

Figure 4:
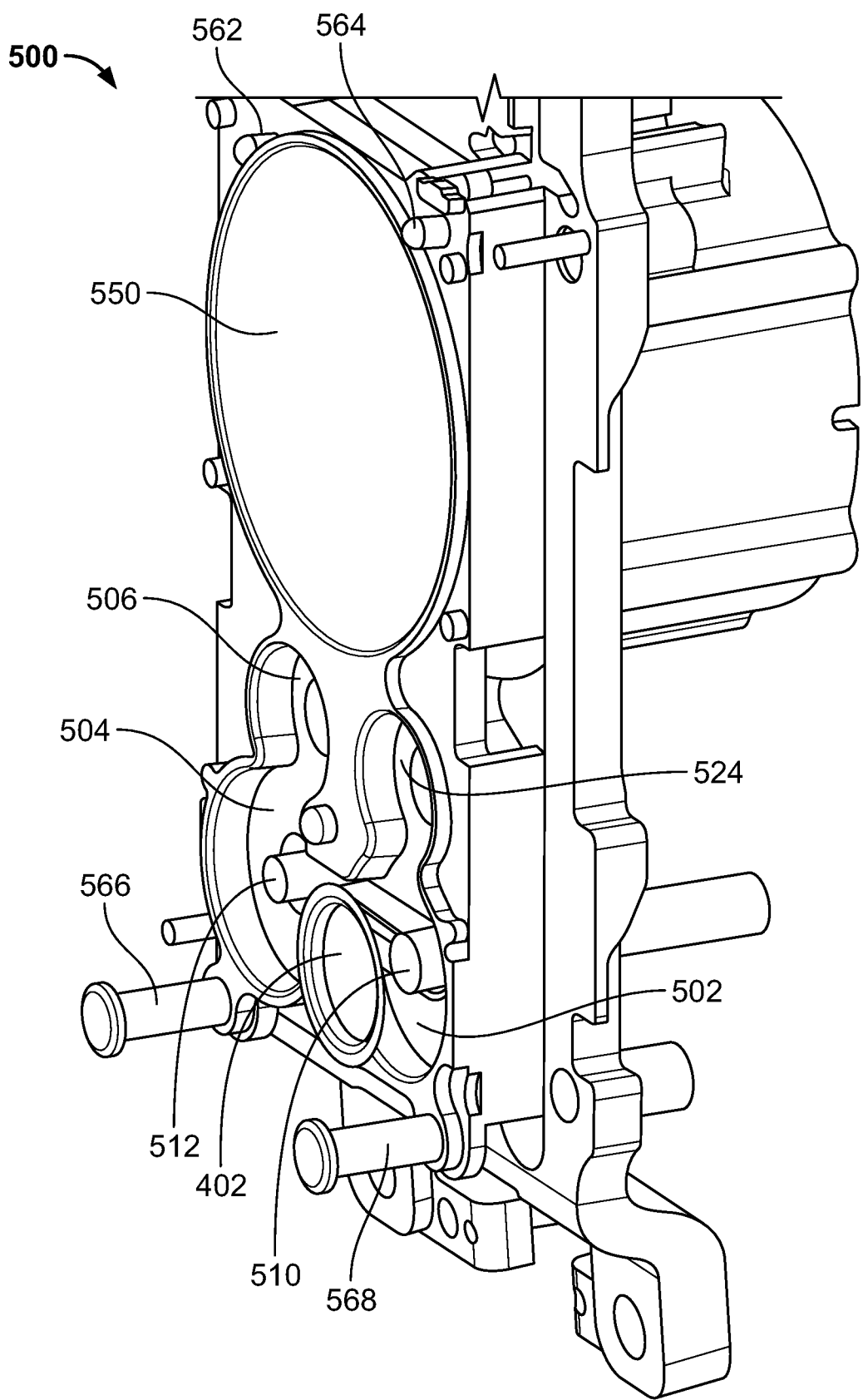
FIG. 4 illustrates examples of a diaphragm and a fluidics module that is part of an ophthalmic surgical console that may be used in systems and methods in accordance with the present disclosure.

FIG. 4 illustrates the diaphragm 402 and a fluidics module 500 that is part of the ophthalmic surgical console 100 that may be used in systems and methods in accordance with the present disclosure. The fluidics module 500 is designed to accept the cassette 314 and to interact with the cassette 314 as part of the fluidics system 200. The fluidics module 500 has lugs 562, 564 that align with the holes 462, 464 of the cassette 314 and lugs 566, 568 that align with the notches 466, 468 of the cassette 314 for loading the cassette 314 into the console 100.

The fluidics module 500 has a pump housing area 550 for accommodating mechanics of the pump 322 for interacting with the arcuate elastomeric channel cover 454 of the cassette 314. The fluidics module 500 has areas 506, 524 for accommodating the irrigation valve 306 and vent valve 324, respectively. The fluidics module 500 further has areas 502, 504 for accommodating the diaphragms 402, 404, respectively. The areas 502, 504 may be shaped and sized in accordance with the diaphragms 402, 404, respectively. For example, the diaphragms 402, 404 may be circular, and the areas 502, 504 may be circular. The fluidics module 500 may have a non-conductive pressure sensor coil housing 510 for housing the coil of pressure sensor 600 and/or a non-conductive pressure sensor coil housing 512 for housing the coil of pressure sensor 602. As an alternative, the coil of pressure sensor 600 and/or the coil of pressure sensor 602 may be implemented with traces (e.g., copper or another suitable conductor) on a printed circuit board.

Figure 5:
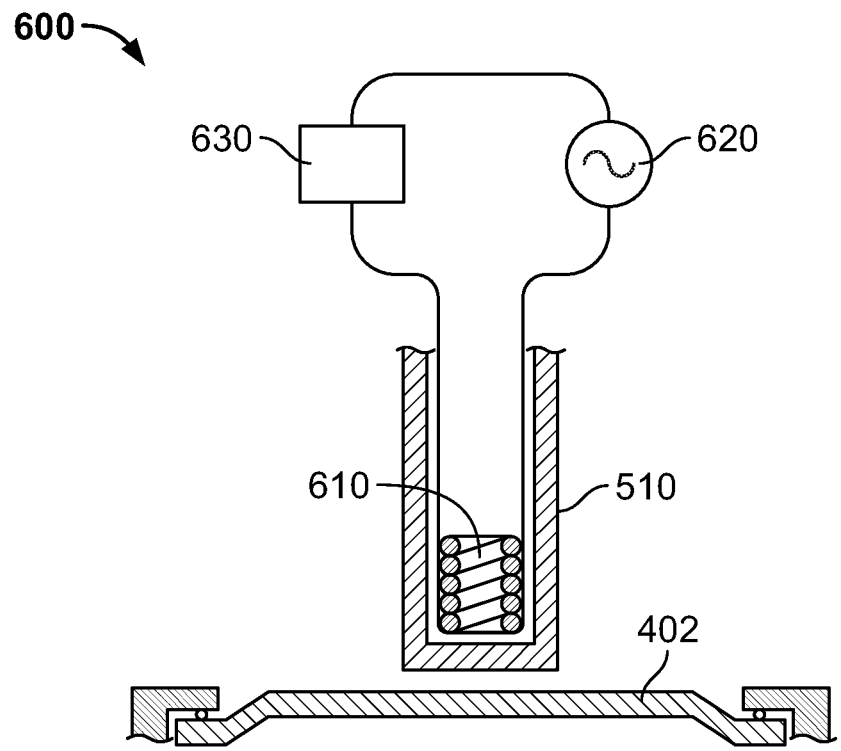
FIG. 5 is a schematic diagram of an example of a pressure sensor that may be used in systems and methods in accordance with the present disclosure.

FIG. 5 is a schematic diagram of an example of a pressure sensor 600 that may be used in systems and methods in accordance with the present disclosure. As shown in FIG. 5, the pressure sensor 600 includes a position sensor that comprises a position sensor coil 610. As will be appreciated by persons of ordinary skill in the art, the position sensor coil 610 is illustrated schematically. In some embodiments, as mentioned above, the position sensor coil 610 (and/or the position sensor coil 612 of pressure sensor 602) may be implemented with traces on a printed circuit board. As can be appreciated from FIGS. 4 and 5 and the disclosure herein, the position sensor is a non-contact sensor, i.e., it is not in physical contact with the diaphragm 402. The position sensor is also not in contact with the fluid being measured, as the diaphragm isolates the fluid from the position sensor.

The diaphragm 402 is a conductive sheet or plate that moves in response to the fluid pressure exerted upon it. For example, the diaphragm 402 may be a thin, metallic material such as stainless steel or another suitable metallic or conductive material. As an example, the diaphragm may be about 0.5 inches in diameter and about 0.003 inches in thickness. Other suitable materials, shapes, and dimensions are possible and contemplated within the scope of the disclosure.

The position sensor coil 610 is a conductive coil that is part of an alternating current circuit. The position sensor coil 610 may be relatively small, for example 2-4 millimeters in diameter and about 0.5 millimeters in height, although other suitable dimensions are possible and contemplated within the scope of the disclosure.

The system further includes a source of alternating current and high frequency oscillator 620 and a measurement device 630, which may comprise signal conditioning circuitry that measures the impedance, inductance, or resonant frequency changes of the position sensor coil 610, for making measurements as described below. The high frequency oscillator generates a suitable frequency for the purposes described herein, e.g., 2 MHz or any other suitable frequency. The position sensor coil 610 is connected to the remainder of the circuit through leads. When the position sensor coil 610 is activated by the high frequency oscillator, it generates a magnetic field due to the current flowing through the coil.

Figure 6:
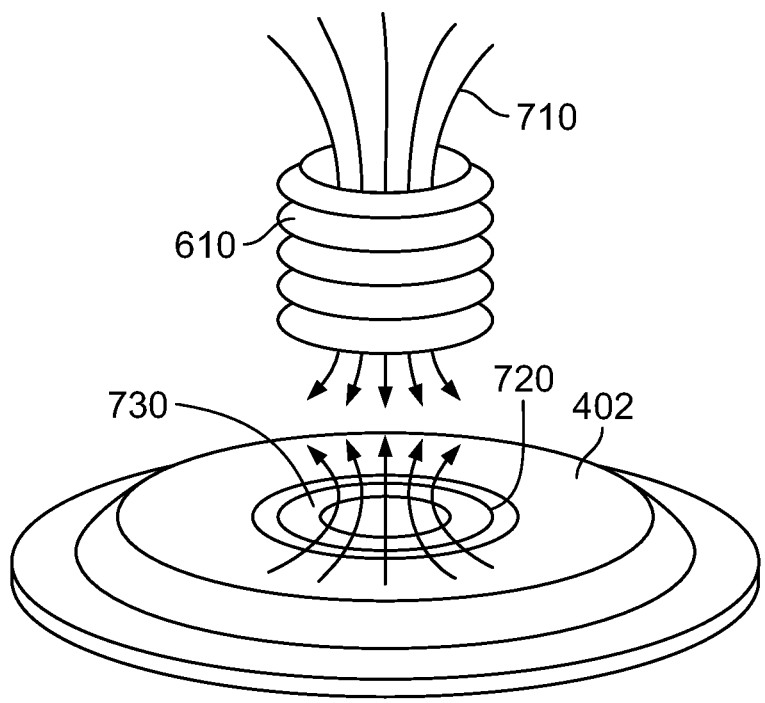
FIG. 6 is a schematic diagram of the pressure sensor of FIG. 6 showing the magnetic fields and induced eddy currents.

The pressure sensor 600 operates as an eddy current pressure sensor. FIG. 6 is a schematic diagram of the pressure sensor 600 of FIG. 5 showing the magnetic fields and induced eddy currents. When the position sensor coil 610 is activated by alternating current, it generates magnetic field 710 as shown. This magnetic field 710 induces local electric currents in the form of eddy currents 720 within the conductive diaphragm 402, which is in close proximity to the position sensor coil 610. The eddy currents 720 generate a magnetic field 730 that is opposite to the magnetic field 710. The eddy currents 720 and resulting magnetic field 730 cause a change in the inductance or impedance or resonant frequency of the position sensor coil 610.

As can be appreciated from FIG. 3, the diaphragm 402 is in contact with fluid being aspirated from the eye through the aspiration line. The diaphragm 402 is non-invasive and isolates the fluid from the remainder of the pressure sensor 600. As the fluid pressure changes on the diaphragm 402, the position of the diaphragm 402 changes slightly in response to the pressure changes. Consequently, the position of the diaphragm 402 changes with respect to the fixed position of the position sensor coil 610. These position changes result in different eddy currents 720 and different magnetic fields 730, which in turn result in differences in inductance or impedance or resonant frequency of the pressure sensor coil 610.

The measurement device 630 is a capable of measuring the changes in inductance or impedance or resonant frequency of the position sensor coil 610. The signal conditioning electronics sense inductance or impedance or resonant frequency variation as the gap between the diaphragm 402 and the position sensor coil 610 changes. The signal conditioning electronics translate this variation into a usable displacement signal, i.e., from these measurements, the position sensor is used to determine the position of the diaphragm 402. The signal conditioning electronics may comprise available electronics, such as the LDC 1614 Inductance to Digital Converter available from Texas Instruments. By calibrating the determined positions with fluid pressure, a correlation is established by which the fluid pressure is determined based upon the measurements of the measurement device 630. Thus, the eddy current pressure sensor 600 is used to determine the fluid pressure acting on the diaphragm 402.

While pressure sensor 600 has been illustrated as a pressure sensor for the aspiration fluid, an eddy current pressure sensor as disclosed herein may also be used as a pressure sensor 602 for the irrigation fluid. For example, in FIGS. 5 and 6, the diaphragm 402 may be the diaphragm 404, the pressure sensor 600 may be the pressure sensor 602, and the position sensor coil 610 may be the position sensor coil 612 (as illustrated schematically in FIG. 2). The diaphragm 404 may be similar to the diaphragm 402 as described herein, and the pressure sensor 602 for the irrigation fluid may be designed and operated as described herein with respect to the pressure sensor 600 for the aspiration fluid. If two or more eddy current pressure sensors as described herein are used in the same system (e.g., one for aspiration fluid and one for irrigation fluid), it may be desirable to operate the different sensors at different frequencies so as to avoid interference.

The use of eddy current pressure sensor 600 and/or 602 in an ophthalmic surgical system as disclosed herein enables the measurement of fluid pressure in an ophthalmic procedure in a non-contact, non-invasive manner. This system provides advantages over prior ophthalmic surgical systems which used load cell sensors in a contact method, in contact with the diaphragm, which have the potential for drawbacks of a limited frequency response and relatively high hysteresis in addition to potential additional protection needed for the sensor to satisfy safety requirements. In addition, the use of eddy current pressure sensor 600 and/or 602 in an ophthalmic surgical system as disclosed herein provides advantages over prior ophthalmic surgical systems which used optical pressure sensors, which have the potential for drawbacks due to sensitivity to optical alignment and/or surface finish variations of the diaphragm. The use of eddy current pressure sensor 600 and/or 602 in an ophthalmic surgical system as disclosed herein does not require narrow beam light generation, complex optical alignments, or high speed image processing, as has been needed in prior optical pressure sensors in ophthalmic surgical systems. Instead, the use of eddy current pressure sensor 600 and/or 602 in an ophthalmic surgical system as disclosed herein offers a faster response and simple implementation.

The use of eddy current pressure sensor 600 and/or 602 in an ophthalmic surgical system as disclosed herein is also advantageous as being compact in size and simple to operate. The position sensor has no direct contact with the diaphragm. The position sensor does not require a sharp optical image on the diaphragm. Both the sensor and the control electronics may be temperature compensated during the manufacturing process and further compensated during the runtime.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:
1. An ophthalmic surgical system comprising:
a handpiece with a working tip for performing an ophthalmic surgical procedure inside an eye;
an irrigation system for delivering irrigation fluid to the eye during the ophthalmic surgical procedure, the irrigation system comprising an irrigation source, an irrigation path in the handpiece, and irrigation tubing between the irrigation source and the irrigation path in the handpiece;
an aspiration system for aspirating aspiration fluid from the eye during the ophthalmic surgical procedure, the aspiration system comprising an aspiration path in the handpiece, aspiration tubing extending from the aspiration path in the handpiece, and a pump for providing suction through the aspiration tubing and aspiration path in the handpiece; and a pressure sensor system in communication with one of the irrigation path or the aspiration path, the pressure sensor system comprising:
  a conductive, movable diaphragm having a first side opposite a second side, the first side of the diaphragm facing a flow path for one of the aspiration fluid being aspirated from the eye or the irrigation fluid being delivered to the eye, wherein the diaphragm is configured to move in response to fluid pressure in the flow path, the fluid pressure being exerted on the first side of the diaphragm; and
  an eddy current position sensor in communication with the diaphragm without contacting the diaphragm, the eddy current position sensor comprising a position sensor coil activatable by high frequency alternating current and signal conditioning electronics capable of sensing variation in inductance, impedance, or resonant frequency in the position sensor coil as a gap between the second side of the diaphragm and the position sensor coil changes in response to the fluid pressure in the flow path and of translating that variation into a displacement signal correlated to the fluid pressure in the flow path.

2. An ophthalmic surgical system as in claim 1, wherein the signal conditioning electronics are capable of sensing inductance in the position sensor coil.

3. An ophthalmic surgical system as in claim 1, wherein the signal conditioning electronics are capable of sensing impedance in the position sensor coil.

4. An ophthalmic surgical system as in claim 1, wherein the signal conditioning electronics are capable of sensing resonant frequency in the position sensor coil.

5. An ophthalmic surgical system as in claim 1, wherein the first side of the diaphragm faces a flow path for aspiration fluid being aspirated from the eye.

6. An ophthalmic surgical system as in claim 1, wherein the first side of the diaphragm faces a flow path for irrigation fluid being delivered to the eye.

7. An ophthalmic surgical system as in claim 1, wherein the position sensor coil is housed in a non-conductive housing.

8. An ophthalmic surgical system as in claim 1, further comprising a high frequency oscillator for activating the position sensor coil at a high frequency.

9. An ophthalmic surgical system comprising a fluidics module in combination with a fluidics cassette, the fluidics module and fluidics cassette together comprising:
  an irrigation flow path through which irrigation fluid is delivered to an eye during an ophthalmic surgical procedure;
  an aspiration flow path through which aspirated fluid is aspirated from the eye during the ophthalmic surgical procedure; and
  a pressure sensor system in communication with a flow path, wherein the flow path is one of the irrigation flow path or the aspiration flow path, the pressure sensor system comprising:
    a conductive, movable diaphragm having a first side opposite a second side, the first side of the diaphragm facing the flow path, wherein the diaphragm is configured to move in response to fluid pressure in the flow path, the fluid pressure being exerted on the first side of the diaphragm; and
    an eddy current position sensor positioned in communication with the diaphragm without contacting the diaphragm, the eddy current position sensor comprising a position sensor coil activatable by high frequency alternating current and signal conditioning electronics capable of sensing variation in inductance, impedance, or resonant frequency in the position sensor coil as a gap between the diaphragm and the position sensor coil changes in response to the fluid pressure in the flow path and of translating that variation into a displacement signal correlated to the fluid pressure in the flow path.

10. An ophthalmic surgical system as in claim 9, wherein the signal conditioning electronics are capable of sensing inductance in the position sensor coil.

11. An ophthalmic surgical system as in claim 9, wherein the signal conditioning electronics are capable of sensing impedance in the position sensor coil.

12. An ophthalmic surgical system as in claim 9, wherein the signal conditioning electronics are capable of sensing resonant frequency in the position sensor coil.

13. An ophthalmic surgical system as in claim 9, wherein the first side of the diaphragm faces the aspiration flow path.

14. An ophthalmic surgical system as in claim 9, wherein the first side of the diaphragm faces the irrigation flow path.

15. An ophthalmic surgical system as in claim 9, wherein the position sensor coil is housed in a non-conductive housing.

16. An ophthalmic surgical system as in claim 9, further comprising a high frequency oscillator for activating the position sensor coil at a high frequency.

17. A method of measuring fluid pressure in an ophthalmic surgical system, the method comprising:
  passing fluid through a fluid flow path during an ophthalmic surgical procedure, wherein a conductive, movable diaphragm having a first side opposite a second side is positioned with the first side of the diaphragm facing the fluid flow path, and wherein the fluid flow path is for one of aspiration fluid being aspirated from an eye or irrigation fluid being delivered to the eye;
  activating a position sensor coil by high frequency alternating current, wherein:
    the position sensor coil is in communication with the diaphragm without contacting the diaphragm; and
    the diaphragm is configured to move in response to fluid pressure in the fluid flow path, the fluid pressure being exerted on the first side of the diaphragm;
  sensing variation of inductance or impedance or resonant frequency in the position sensor coil as a gap between the second side of the diaphragm and the position sensor coil changes due to the fluid pressure in the fluid flow path; and
  translating that variation into a displacement signal correlated to the fluid pressure in the fluid flow path.

18. A method of measuring fluid pressure in an ophthalmic surgical system as in claim 17, wherein the step of sensing variation of inductance or impedance or resonant frequency in the position sensor coil comprises sensing inductance variation in the position sensor coil.

19. A method of measuring fluid pressure in an ophthalmic surgical system as in claim 17, wherein the step of sensing variation of inductance or impedance or resonant frequency in the position sensor coil comprises sensing impedance variation in the position sensor coil.

20. A method of measuring fluid pressure in an ophthalmic surgical system as in claim 17, wherein the step of sensing variation of inductance or impedance or resonant frequency in the position sensor coil comprises sensing resonant frequency variation in the position sensor coil.

* * * * *